(12) United States Patent
Houde

(10) Patent No.: US 7,258,681 B2
(45) Date of Patent: Aug. 21, 2007

(54) ANGIOGRAPHIC FLUID CONTROL SYSTEM

(75) Inventor: Eric Houde, Saratoga Springs, NY (US)

(73) Assignee: Scimed Life Systems, Inc., Maple Grove, MN (US)

( * ) Notice: Subject to any disclaimer, the term of this patent is extended or adjusted under 35 U.S.C. 154(b) by 78 days.

(21) Appl. No.: 10/262,924

(22) Filed: Oct. 2, 2002

(65) Prior Publication Data

US 2003/0125618 A1 Jul. 3, 2003

Related U.S. Application Data

(60) Provisional application No. 60/326,940, filed on Oct. 4, 2001.

(51) Int. Cl.
A61M 5/00 (2006.01)
A61M 1/00 (2006.01)
A61M 37/00 (2006.01)
A61M 31/00 (2006.01)

(52) U.S. Cl. .......... 604/246; 604/30; 604/131; 604/500

(58) Field of Classification Search .......... 604/30, 604/65, 82, 246, 131, 151, 500; 600/431, 600/432, 435
See application file for complete search history.

(56) References Cited

U.S. PATENT DOCUMENTS

| | | | |
|---|---|---|---|
| 3,749,285 A * | 7/1973 | Latham, Jr. | 222/58 |
| 5,207,642 A * | 5/1993 | Orkin et al. | 604/65 |
| 5,254,092 A | 10/1993 | Polyak | |
| 5,356,375 A | 10/1994 | Higley | |
| 5,378,229 A | 1/1995 | Layer et al. | |
| 5,515,851 A | 5/1996 | Goldstein | |
| 5,562,614 A | 10/1996 | O'Donnell | |
| 5,640,995 A | 6/1997 | Packard et al. | |
| 5,730,731 A | 3/1998 | Mollenauer et al. | |
| 5,800,383 A | 9/1998 | Chandler et al. | |
| 5,806,519 A | 9/1998 | Evans, III et al. | |
| 5,830,180 A | 11/1998 | Chandler et al. | |
| 5,840,026 A | 11/1998 | Uber, III et al. | |
| 6,063,052 A | 5/2000 | Uber, III et al. | |
| 6,083,205 A | 7/2000 | Bourne et al. | |
| 6,099,511 A | 8/2000 | Devos et al. | |
| 6,110,144 A | 8/2000 | Choh et al. | |
| 7,094,216 B2 * | 8/2006 | Trombley et al. | 604/65 |

* cited by examiner

*Primary Examiner*—Kevin C. Sirmons
*Assistant Examiner*—Bhisma Mehta
(74) *Attorney, Agent, or Firm*—Miller, Matthias & Hull

(57) ABSTRACT

An automated fluid control system for controlling fluid flow between a catheter, a saline supply, a contrast supply and an injector is disclosed. Pinch valves are provided in the saline input and output lines and contrast input and output lines. A controller is linked to the pinch valves to sequentially open and close the pinch valves during functions which include contrast injection and saline injection.

30 Claims, 1 Drawing Sheet

ANGIOGRAPHIC FLUID CONTROL SYSTEM

CROSS-REFERENCE TO RELATED APPLICATION

This application claims the benefit under 35 U.S.C. § 119(e) of U.S. provisional patent application Ser. No. 60/326,940 filed Oct. 4, 2001, the disclosure of which is incorporated herein by reference.

TECHNICAL FIELD

A fluid control system is disclosed for controlling fluid flow in an angiographic apparatus. More specifically, a fluid control system is disclosed for controlling fluid flow between a catheter, a saline supply, a waste dump, a contrast supply and an injector.

BACKGROUND OF THE RELATED ART

Various medical procedures involve the introduction of fluids into the body of a patient using a catheter. When a series of different fluids are to be administered, it is often necessary to flush one fluid from the catheter before the next fluid is administered. For example, during angioplasty, the catheter is often flushed with saline before and/or after the addition of contrast solution. Further, it is also necessary to purge any injection lines of air and to prevent the reintroduction of air into the lines.

Accordingly, it is often necessary to selectively connect a catheter to any one of a number of fluid sources such as a contrast solution source, saline source and a waste dump. Further, it is often necessary to connect the catheter to a pressure transducer to monitor the intravascular pressure during a procedure.

The most commonly used apparatus for these types of procedures involves the connection of a catheter to a manifold which consists of a plurality of stopcock valves connected in a series. While one of the stopcocks is connected to the catheter, the other stopcocks are connected to fluid supplies, a pressure transducer, an injection mechanism or other equipment. The physician is required to selectively open and close the stopcock valves during the procedure.

Because a physician is required to manipulate a number of stopcock valves during a procedure to achieve a desired flow path to or from the catheter, it takes a considerable degree of training to learn how to properly operate one of the prior art manifolds. Further, because it is not immediately evident from looking at the manifold which way the fluid is flowing, it is easy to make an improper connection resulting in a high-pressure fluid being applied to a pressure transducer, causing damage to or malfunction of the transducer.

Because a number of stopcock valves are involved in these manifolds, the handles must be small so as to not cause interference with one another. However, the small handles can be difficult to grasp and manipulate.

Another problem associated with currently available manifolds is the use of a single output conduit which is connected to the catheter. Because contrast, saline and, possibly, waste are all passed through the single conduit or line, flushing is required between numerous functions. As a result, contrast can often be wasted because there is no way to "save" the contrast once it has been injected into the manifold. Further, if waste material is drawn into the manifold, saline is wasted as the manifold is flushed. Further, it is time consuming to flush the manifold between functions.

Finally, because currently available manifolds are equipped with a pressure transducer, adjacent the injector, which may be a syringe or power injector, the pressure readings are compromised due to waveform dampening that occurs in the manifold. In other words, pressure waveforms must travel through the fluid line of the manifold and connecting lines between the manifold, catheter and injector. Typically, the total length of conduit between the injector and the catheter is about 48 inches. As a result of the waveforms having to travel through this extensive length of conduit, substantial dampening occurs, thereby compromising the pressure readings.

As a result, there is a need for an improved fluid control system which is easier for the physician to manipulate.

SUMMARY OF THE DISCLOSURE

In satisfaction of the aforenoted needs, a fluid control system is disclosed for controlling fluid flow between a catheter, a saline supply, a contrast supply and an injector. The system comprises a saline input line coupling the saline supply to the injector. The saline input line passes through a saline input pinch valve. The system also comprises a contrast input line coupling the contrast supply to the injector. The contrast input line passes through a contrast input pinch valve. A saline output line couples the catheter to the injector. The saline output line passes through a saline output pinch valve. A contrast output line couples the catheter to the injector. The contrast output line passes through a contrast input pinch valve.

The system further comprises means for opening and closing the various pinch valves to provide the desired fluid flow. Specifically, the system comprises a means for closing the saline input and output pinch valves while opening the contrast input and output pinch valves. As a result, contrast may be drawn into the injector and directed out to the catheter. The system further comprises a means for closing the contrast input and output pinch valves while opening the saline input and output pinch valves. As a result, saline may be drawn into the injector from the saline supply and directed out to the catheter.

In a refinement, lines are provided for removing waste from the catheter and passing the waste to a waste dump or waste reservoir. In such a refinement, the system comprises a waste output line that couples the waste dump to the injector. The waste output line passes through a waste output pinch valve. The system also comprises a waste input line that couples the catheter to the injector. The waste input line passes through a waste input pinch valve. The system also comprises a means for closing the contrast input and output pinch valves and the saline input and output pinch valves while opening the waste input and output pinch valves. As a result, waste may be drawn in from the catheter to the injector and directed out to the waste dump. In this refinement, the waste input and output pinch valves are closed while contrast is drawn into the injector and directed out to the catheter. Further, in this refinement, the waste input and output pinch valves are closed while saline is drawn into the injector and directed out to the catheter.

In a refinement, a controller is provided for opening and closing the various pinch valves. The controller comprises a memory with at least two stored functions including a contrast function and a saline function. When switched to the contrast function, the controller closes the saline input and output pinch valves and opens the contrast input and output pinch valves. As a result, suction can be applied at the injector to drawn contrast in from the contrast supply through the contrast input line and into the injector. The contrast then may be directed toward the catheter by applying positive displacement pressure from the injector pushing the contrast through the contrast output line to the catheter. Similarly, when switched to the saline function, the controller closes the contrast input and output pinch valves while opening the saline input and output pinch valves. As a result, saline can be drawn into the catheter from the saline supply and saline input line and then directed out towards the catheter through the saline output line.

In a further refinement of this concept, waste input and output lines are provided along with waste input and output pinch valves. The waste input and output pinch valves are also coupled to the controller. The controller also includes a stored waste function. When switched to the waste function, the controller closes the contrast input and output pinch valves and the saline input and output pinch valves while opening the waste input and output pinch valves. As a result, suction applied at the injector causes waste to be drawn in from the catheter to the injector which then directs the waste outward through the waste output line to the waste dump. In this refinement, when switched to the contrast function, the controller also closes the waste input and output pinch valves and, when switched to the saline function, the controller also closes the waste input and output pinch valves.

In a further refinement, the opening and closing of the input and output valves in the saline, contrast and waste functions may be sequential. For example, in the saline function, the saline output pinch valve may remain closed while the saline input pinch valve is opened and saline is drawn into the injectors. Then, with the injector loaded with saline, the saline input pinch valve may be closed and the saline output pinch valve opened as the saline is ejected from the injector towards the catheter. An analogous sequence may be followed for the contrast function and, in a refinement that includes a waste function, the sequential concept may also be applied to the waste input and output pinch valves.

In a further refinement, a control panel is linked to the controller. The control panel includes readily identifiable switches or buttons including one clearly marked "contrast," one clearly marked "saline" and, if a waste function is included, one clearly marked "waste" or other suitable indicia to facilitate to operation of the system. Separate buttons may be provided or a single switch with clearly marked "contrast" and "saline" positions may be provided. Again, if a waste function is provided, the switch would also include a clearly marked "waste" position.

In a further refinement, a number of one-way check valves are provided to ensure proper fluid flow. Specifically, a one-way check valve is provided in the saline input line which enables flow from the saline supply towards the injector, but not vice versa. A one-way check valve may also be provided in the contrast input line which enables fluid flow from the contrast towards the injector, but not vice versa. Also, a one-way check valve may be provided in the contrast output line which enables flow from the injector towards the catheter, but not vice versa. Finally, a one-way check valve may be provided in the saline output line which enables flow from the injector towards the catheter, but not vice versa.

In a refinement that includes a waste function, a one-way check valve is provided in the waste output line which enables flow towards the waste dump but not back towards the injector. A one-way check valve may also be provided in the waste input line from the catheter which enables flow from the catheter towards the injector, but not vice versa.

In another refinement, a pressure transducer is coupled to the catheter with a transducer protection valve disposed therebetween that is linked to the controller. In the saline function, the controller closes the pressure transducer protection valve to protect the pressure transducer from the high pressure event of injecting saline. Optionally, the pressure transducer protection valve may also be closed during the contrast function where contrast is injected into the catheter. As another option, the pressure transducer protection valve may be closed during both the saline and contrast functions.

In another refinement, a fluid control system is provided whereby a pressure transducer is coupled directly to or closely adjacent to the proximal end of the catheter for improved pressure reading.

One or more stopcock ports may be incorporated into the system to facilitate the injection of medicaments. For example, a stopcock may be disposed in the contrast input line. Preferably, the stopcock includes an injection port for the for injection of medicaments. Similarly, a stopcock may be disposed between the catheter and the injector. Again, an injection port is preferable to facilitate the injection of medicaments.

DETAILED DESCRIPTION OF THE PRESENTLY PREFERRED EMBODIMENTS

Figure 1:
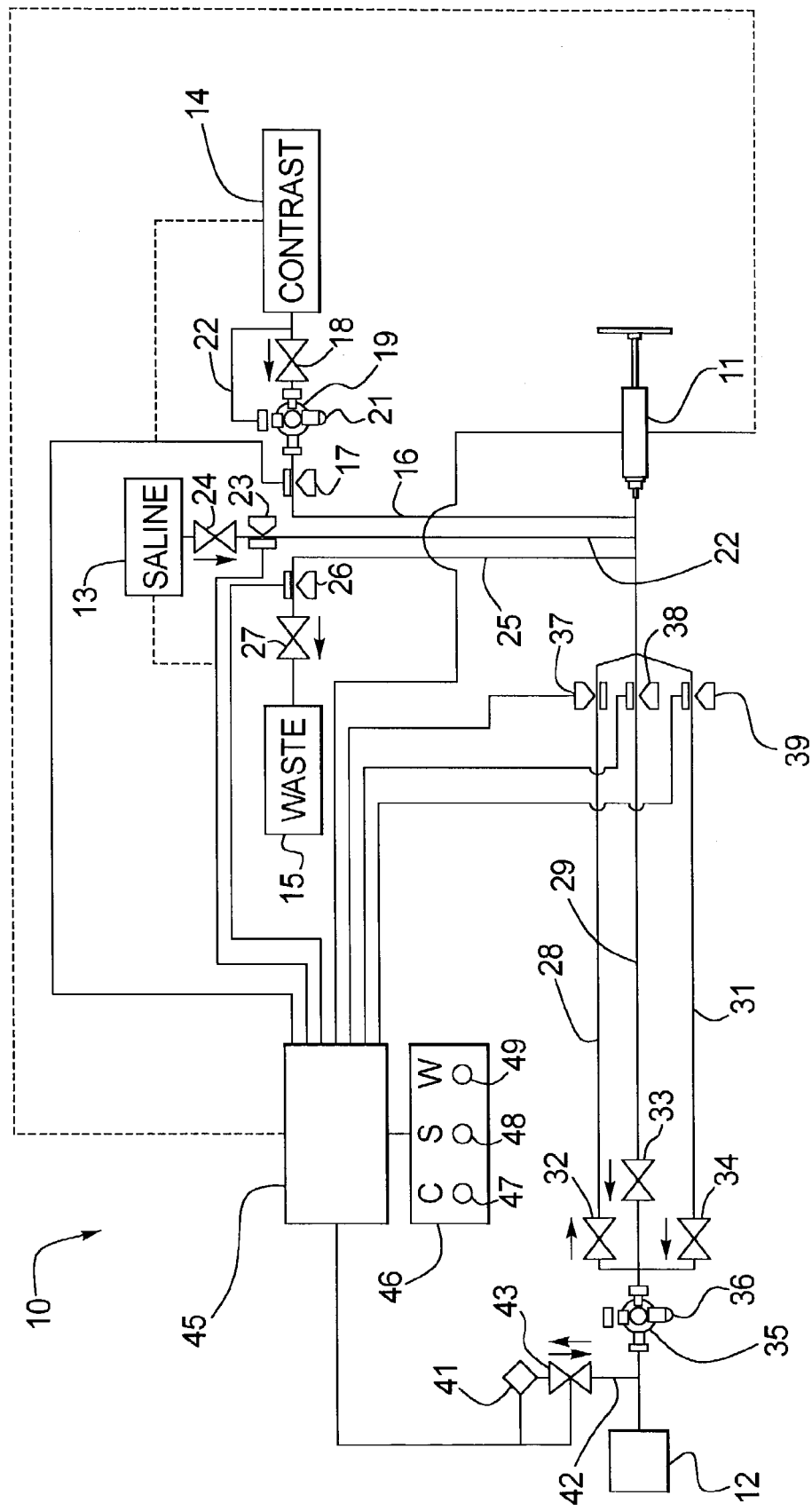
FIG. 1 illustrates, schematically, a disclosed fluid control system.

A fluid control system 10 includes an injector 11 and a catheter shown schematically at 12. Two primary fluids are injected into the catheter-saline from the saline supply 13 and contrast from the contrast supply 14. In the embodiment 10 shown in FIG. 1, waste fluid is also drawn in from the catheter 12 and deposited in the waste dump 15.

The contrast supply 14 is coupled to a contrast supply line 16. The contrast supply line 16 passes through a contrast input pinch valve 17. The contrast supply line 16 may also pass through a one-way check valve 18, the function of which will be described later. Similarly, to facilitate the injection of medicaments into the system, a stopcock 19 is disposed in the contrast input line 16. The stopcock 19 preferably includes an injection port 21. A bypass line 22 may also be provided to bypass the one-way check valve 18. The bypass line 22 can be used to save unneeded clean contrast solution by injecting it back into the contrast supply 14.

The saline supply 13 is also linked to a saline input line 22. The saline input line 22 passes through a pinch valve 23 as well as a one-way check valve 24. The waste dump is linked or coupled to a waste output line 25 which also passes through a pinch valve 26 and a one-way check valve 27. A separate waste input line 28, contrast output linen 29 and saline output line 31 are provided. The waste input line is also preferably provided with a one-way check valve 32 which permits flow from the catheter 12 to the injector 11 and not vice versa. A one-way check valve 33 is provided in the contrast output line which permits flow from the injector 11 to the catheter 12 and not vice versa. Similarly, a one-way check valve 34 may be provided in the saline output line which permits flow from the injector 11 to the catheter 12 and not vice versa. Optionally, a stopcock 35 may be disposed between the injector 11 and catheter 12. Preferably, the stopcock includes an injection port 36 for adding medicaments to the system. The waste input line 28 passes through a pinch valve 37. Similarly, the contrast output line passes through a pinch valve 38 and the saline output line passes through a pinch valve 39.

To monitor pressure in the catheter 12, a pressure transducer 41 is provided which is linked to the catheter 12 through a pressure transducer line 42. To protect the transducer against high pressure injection events, a pressure transducer protection valve 43 is provided.

The system 10 is preferably operated with a controller 45. As shown in FIG. 1, the controller 45 is linked to the contrast input pinch valve 17, the saline input pinch valve 23, the waste output pinch valve 26, the waste input pinch valve 37, the contrast output pinch valve 38 and the saline output pinch valve 39. A control panel 46 may be provided with a switching mechanism to switch the controller between the contrast, saline and waste functions. A preferred embodiment includes a contrast button 47, a saline button 48 and, optionally, a waste button 49. Another preferred embodiment includes a single switch with clearly marked "saline" and "contrast" positions. Again, if a waste function is provided, a "waste" position would also be provided.

When the waste button 49 is pressed, the controller 45 opens the waste input pinch valve 37 and waste output pinch valve 26. The injector may then draw waste material in from the catheter 12, through the waste input line 28 before ejecting it out through the waste output line 25 to the waste dump 15. At this point, the controller 45 has closed the contrast output pinch valve 38, the saline output pinch valve 39, the saline input pinch valve 23 and the contrast output pinch valve 17. However, if the contrast input one-way check valve 18 and the saline input one-way check valve 24 are provided as shown in FIG. 1, closure of the pinch valves 18 and 23 is not absolutely necessary. In the alternative, incorporation of the one-way check valves 18 and 24 are not necessary if the pinch valve 17 and 23 are in the closed position during the waste function.

When the saline button 48 is pressed, the controller 45 opens the saline input pinch valve 23 and saline output pinch valve 39 and closes contrast input pinch valve 17, the waste input pinch valve 37 and the contrast output pinch valve 38. The waste output pinch valve 26 may also be closed by the controller 45. However, if a one-way waste output check valve 27 is provided, closure of the pinch valve 26 is not necessary. In the alternative, the one-way check valve 27 may not be necessary if the pinch valve 26 is closed during the saline function. With the saline input pinch valve 23 open, saline may then be drawn in from the saline reservoir 13 to the injector 11. The saline may then be expelled out through the saline output line 31 as the saline output pinch valve 39 is open.

When the contrast button 47 is pushed, the controller 45 opens the contrast input pinch valve 17 and the contrast output pinch valve 38 and closes the saline input pinch valve 23 and saline output pinch valve 39. If the one-way check valves 27 and 32 in the waste output and input lines 25 and 28, respectively, are not provided, the waste output pinch valve 26 and waste input pinch valve 37 are also closed by the controller 45. Contrast may then be drawn in from the contrast reservoir 14 through the contrast input line 16 to the injector. It may then be pumped the catheter 12 through the contrast output line as the contrast output pinch valve 38 is open.

As noted above, the inclusion of the check valves 18, 24, 27, 32, 33 and 34 may eliminate the need for the opening or closure of certain pinch valves during the contrast, saline and waste functions. However, to preserve contrast and saline fluid and to reduce the amount of contamination in the saline and contrast fluids being sent to the catheter 12, use of the check valve is advisable. Further, incorporation of the check valves may also provide an added safety measure in the event certain pinch valves fail.

Further, sequential opening and closing of pinch valves during the contrast, saline and waste functions may also be advisable. For example, when the contrast button 47 is pushed, in the contrast function, all pinch valves may be closed with the exception of the contrast input pinch valve 17. Contrast may be then drawn into the injector 11. Then, the contrast input pinch valve 17 may be closed and only the contrast output pinch valve 38 open for injection of the contrast through the contrast output line 29 to the catheter 12. Similarly, in the saline function, all pinch valves may be closed with the exception of the saline input pinch valve 23. Saline may then be drawn into the injector 11 before closing the saline input pinch valve 23. Then, the saline output pinch valve 39 may be opened for injection of saline through the saline output line 31 to the catheter 12. Similarly, when the waste button 49 is pressed, in the waste function, all pinch valves may be closed with the exception of the waste input pinch valve 37. Waste is then drawn into the injector 11 before closing the waste input pinch valve 37 and opening the waste output pinch valve 26 for pumping the waste through the waste output line 25 to the waste dump 15.

The controller may also open and close the pressure transducer protection valve during certain functions. For example, during injection of saline or contrast, it may be advisable to close the pressure transducer protection valve 43 so as to not expose the pressure transducer 41 to any high pressure events. This function may also be performed by the controller 45. It will also be noted that the injection of medicaments through the injection port 21 and/or through the injection port 36 may be controlled by the controller 45.

As shown, the injector 11 may be a manual injector or may be a pump that is controlled by the controller 45. If the injector is a manual syringe, the use of the one-way check valves 18, 24, 27, 32, 33 and 34 may be preferable as an integral part of the system 10. Further, the controller 45 may also monitor the fluid levels in the contrast supply reservoir 14, the saline supply reservoir 13 and/or the waste dump 15. The controller 45 may also monitor the pressure in the catheter 12 by being linked to the pressure transducer 41 as shown.

Thus, an improved fluid control system is provided for angiographic procedures. A single switch, with clearly marked "saline," "contrast" and, optionally, "waste" positions or, buttons 47, 48 and 49 may be provided and the manipulation of numerous stopcocks is avoided. Other function selection mechanisms will be apparent to those skilled in the art. Those skilled in the art will recognize that many changes may be made in form and detail without departing from the spirit and scope of this disclosure. As it is intended that the foregoing detailed description be regarded as illustrative rather than limiting, it is the following claims, including all equivalents thereof, which are intended to define the scope of the invention.

What is claimed is:

1. A fluid control system for controlling fluid flow between a catheter, a saline supply, a contrast supply and an injector, the fluid control system comprising:
   a saline input line coupling the saline supply to the injector, the saline input line passing through a saline input pinch valve,
   a contrast input line coupling the contrast supply to the injector, the contrast input line passing through a contrast input pinch valve, a saline output line coupling the catheter to the injector, the saline output line passing through a saline output pinch valve, a contrast output line coupling the catheter to the injector, the contrast output line passing through a contrast output pinch valve, a controller for opening and closing the pinch valves, the controller comprising a memory with at least two stored functions including a contrast function and a saline function, when switched to the contrast function, the controller closing the saline input and output pinch valves while opening the contrast input and output pinch valves, when switched to the saline function, the controller closing the contrast input and output pinch valves while opening the saline input and output pinch valves.

2. The fluid control system of claim 1 wherein the contrast input line passes through a one-way check valve that permits flow from the contrast supply to the injector and not vice versa, and the contrast input line passes through a stopcock, the stopcock comprising an injection port, the stopcock being disposed between the contrast input pinch valve and the one-way check valve.

3. The fluid control system of claim 2 further comprising a bypass line coupling the stopcock to the contrast supply.

4. The fluid control system of claim 3 further comprising a stopcock disposed between the catheter and the waste input, contrast output and saline output pinch valves, the stopcock comprising an injection port.

5. The fluid control system of claim 1 further comprising:

a waste output line coupling a waste dump to the injector, the waste output line passing through a waste output pinch valve, a waste input line coupling the catheter to the injector, the waste input line passing through a waste input pinch valve, and wherein the controller further comprises a waste function, when switched to the waste function, the controller closing the contrast input and output pinch valves and the saline input and output pinch valves while opening the waste input and output pinch valves.

6. The fluid control system of claim 5 wherein the waste input line passes through a one-way check valve that permits flow from the catheter to the injector and not vice versa.

7. The fluid control system of claim 5 wherein the waste output line passes through a one-way check valve that permits flow from the injector to the waste dump and not vice versa.

8. The fluid control system of claim 5 wherein the waste input line passes through a one-way check valve that permits flow from the catheter to the injector and not vice versa, the waste output line passes through a one-way check valve that permits flow from the injector to the waste dump and not vice versa, the saline input line passes through a one-way check valve that permits flow from the saline supply to the injector and not vice versa, the saline output line passes through a one-way check valve that permits flow from the injector to the catheter and not vice versa, the contrast input line passes through a one-way check valve that permits flow from the contrast supply to the injector and not vice versa, and the contrast output line passes through a one-way check valve that permits flow from the injector to the catheter and not vice versa.

9. The fluid control system of claim 5 further comprising a control panel linked to a controller that includes a selector mechanism with a first position for switching the controller to the contrast function, a second position for switching the controller to the saline function and a third position for switching the controller to the waste function.

10. The fluid control system of claim 5 further comprising a stopcock disposed between the catheter and the waste input, contrast output and saline output pinch valves, the stopcock comprising an injection port.

11. The fluid control system of claim 1 wherein the contrast input line passes through a stopcock, the stopcock comprising an injection port.

12. The fluid control system of claim 11 wherein the stopcock is disposed between the contrast input pinch valve and the contrast supply.

13. The fluid control system of claim 1 wherein the saline input line passes through a one-way check valve that permits flow from the saline supply to the injector and not vice versa.

14. The fluid control system of claim 1 wherein the saline output line passes through a one-way check valve that permits flow from the injector to the catheter and not vice versa.

15. The fluid control system of claim 1 wherein the contrast input line passes through a one-way check valve that permits flow from the contrast supply to the injector and not vice versa.

16. The fluid control system of claim 1 wherein the contrast output line passes through a one-way check valve that permits flow from the injector to the catheter and not vice versa.

17. The fluid control system of claim 1 further comprising a control panel linked to a controller that includes a selector mechanism with a first position for switching the controller to the contrast function and a second position for switching the controller to the saline function.

18. The fluid control system of claim 1 further comprising a pressure transducer coupled to the catheter and a transducer protection valve disposed therebetween, the transducer protection valve being linked to the controller, in the saline function, the controller closing the pressure transducer protection valve.

19. The fluid control system of claim 1 further comprising a pressure transducer coupled to the catheter and a transducer protection valve disposed therebetween, the transducer protection valve being linked to the controller, in the contrast function, the controller closing the pressure transducer protection valve.

20. The fluid control system of claim 1 further comprising a pressure transducer coupled to the catheter with a transducer protection valve disposed therebetween, the transducer protection valve being linked to the controller, in the contrast and saline functions, the controller closing the pressure transducer protection valve.

21. A fluid control system for controlling fluid flow between a catheter, a saline supply, a waste dump, a contrast supply and an injector, the fluid control system comprising:

a waste output line coupling the waste dump to the injector, the waste output line passing through a waste output pinch valve, the waste output line also passing through a one-way check valve that permits flow from the injector to the waste dump and not vice versa, a saline input line coupling the saline supply to the injector, the saline input line passing through a saline input pinch valve, the saline input line also passing through a one-way check valve that permits flow from the saline supply to the injector and not vice versa, a contrast input line coupling the contrast supply to the injector, the contrast input line passing through a contrast input pinch valve, the contrast input line also passing through a one-way check valve that permits flow from the contrast supply to the injector and not vice versa, a waste input line coupling the catheter to the injector, the waste input line passing through a waste input pinch valve, the waste input line also passing through a one-way check valve that permits flow from the catheter to the injector and not vice versa, a saline output line coupling the catheter to the injector, the saline output line passing through a saline output pinch valve, the saline output line also passing through a one-way check valve that permits flow from the injector to the catheter and not vice versa, a contrast output line coupling the catheter to the injector, the contrast output line passing through a contrast output pinch valve, the contrast output line also passing through a one-way check valve that permits flow from the injector to the catheter and not vice versa, a controller linked to each pinch valve for opening and closing the pinch valves, the controller comprising a memory with at least three stored functions including a contrast function, a saline function and a waste function, a control panel linked to the controller for switching the controller between the at least three stored functions, when switched to the contrast function, the controller closing the saline input and output pinch valves and the waste input and output pinch valves while first opening the contrast input pinch valve and subsequently opening the contrast output pinch valve, when switched to the saline function, the controller closing the contrast input and output pinch valves and the waste input and output pinch valves while first opening the saline input pinch valve and subsequently opening the saline output pinch valve, when switched to the waste function, the controller closing the contrast input and output pinch valves and the saline input and output pinch valves while first opening the waste input pinch valve and subsequently opening the waste output pinch valves.

22. The fluid control system of claim 21 wherein the contrast input line also passing through a stopcock, the stopcock comprising an injection port.

23. The fluid control system of claim 22 wherein the stopcock is disposed between the contrast input pinch valve and the contrast supply.

24. The fluid control system of claim 21 wherein the control panel includes a selector mechanism including a first position for switching the controller to the contrast function, a second position for switching the controller to the saline function and a third position for switching the controller to the waste function.

25. The fluid control system of claim 21 further comprising a pressure transducer coupled to the catheter with a transducer protection valve disposed therebetween, the transducer protection valve being linked to the controller,
in the saline function, the controller closing the pressure transducer protection valve.

26. The fluid control system of claim 21 further comprising a pressure transducer coupled to the catheter with a transducer protection valve disposed therebetween, the transducer protection valve being linked to the controller,
in the contrast function, the controller closing the pressure transducer protection valve.

27. The fluid control system of claim 21 further comprising a pressure transducer coupled to the catheter by a pressure transducer line, with a transducer protection valve disposed therebetween, the transducer protection valve being linked to the controller,
in the contrast and saline functions, the controller closing the pressure transducer protection valve.

28. A fluid control system for controlling fluid flow between a catheter, a saline supply, a contrast supply and an injector, the fluid control system comprising:
a saline input line coupling the saline supply to the injector, the saline input line passing through a saline input pinch valve,
a contrast input line coupling the contrast supply to the injector, the contrast input line passing through a contrast input pinch valve,
a saline output line coupling the catheter to the injector, the saline output line passing through a saline output pinch valve,
a contrast output line coupling the catheter to the injector, the contrast output line passing through a contrast output pinch valve,
a controller closing the saline input and output pinch valves while subsequently opening the contrast input and output pinch valves,
the controller closing the contrast input and output pinch valves while subsequently opening the saline input and output pinch valves.

29. The fluid control system of claim 28 further comprising:
a waste output line coupling a waste dump to the injector, the waste output line passing through a waste output pinch valve,
a waste input line coupling the catheter to the injector, the waste input line passing through a waste input pinch valve,
means for closing the contrast input and output pinch valves and the saline input and output pinch valves while subsequently opening the waste input and output pinch valves.

30. A method for controlling fluid flow in an angiographic apparatus that includes a catheter, a saline supply, a waste dump, a contrast supply and an injector, and a waste output line coupling the waste dump to the injector, the waste output line passing through a waste output pinch valve, a saline input line coupling the saline supply to the injector, the saline input line passing through a saline input pinch valve, a contrast input line coupling the contrast supply to the injector, the contrast input line passing through a contrast input pinch valve, a waste input line coupling the catheter to the injector, the waste input line passing through a waste input pinch valve, a saline output line coupling the catheter to the injector, the saline output line passing through a saline output pinch valve, a contrast output line coupling the catheter to the injector, the contrast output line passing through a contrast output pinch valve, the method comprising:
closing the saline input and output pinch valves and the waste input and output pinch valves while opening the contrast input pinch valve before withdrawing contrast from the contrast supply and into the injector before and opening the contrast output pinch valve and injecting contrast from the injector into the catheter, closing the contrast input and output pinch valves and the waste input and output pinch valves while opening the saline input valve, before withdrawing saline from the saline supply and into the injector before opening the saline output pinch valve and injecting saline from the injector into the catheter, closing the contrast input and output pinch valves and the saline input and output pinch valves while opening the waste input pinch valve before withdrawing waste from the catheter and into the injector before opening the waste output pinch valve and injecting waste from the injector into the waste dump, a waste output line coupling the waste dump to the injector, a saline input line coupling the saline supply to the injector, a contrast input line coupling the contrast supply to the injector, a waste input line coupling the catheter to the injector, a saline output line coupling the catheter to the injector, a contrast output line coupling the catheter to the injector, a controller closing the saline input and output lines and the waste input and output lines while opening the contrast input and output lines, means for closing the contrast input and output lines and the waste input and output lines while opening the saline input and output lines, the controller closing the contrast input and output lines and the saline input and output lines while opening the waste input and output lines.

\* \* \* \* \*